United States Patent [19]

Igarashi et al.

[11] Patent Number: 4,460,722

[45] Date of Patent: Jul. 17, 1984

[54] PROCESS FOR PRODUCING A MICROCAPSULE

[75] Inventors: Yuriko Igarashi; Yoshio Okada, both of Iwaki, Japan

[73] Assignee: Kureha Kagaku Kogyo Kabushiki Kaisha, Nihonbashi, Japan

[21] Appl. No.: 351,598

[22] Filed: Feb. 23, 1982

[30] Foreign Application Priority Data

Mar. 6, 1981 [JP] Japan ................................ 56-32799

[51] Int. Cl.$^3$ ........................... C08K 5/07; C08J 3/10; C08J 3/16
[52] U.S. Cl. .................................. 523/206; 524/501; 524/512; 524/542; 524/597; 524/732; 106/25; 264/4.3; 264/4.7; 427/213.34; 427/213.36; 523/210; 346/215
[58] Field of Search ................... 524/58, 60, 61, 501, 524/512, 542, 597, 732; 106/25; 252/316; 282/27.5

[56] References Cited

U.S. PATENT DOCUMENTS

| | | | |
|---|---|---|---|
| 1,799,954 | 4/1929 | Cherry | 524/732 |
| 3,447,945 | 6/1969 | Mishima et al. | 252/316 |
| 3,516,846 | 6/1970 | Matson | 252/316 |
| 4,107,105 | 8/1978 | Korf | 524/732 |

FOREIGN PATENT DOCUMENTS 2464094 4/1981 France .
2058003 7/1981 United Kingdom .

OTHER PUBLICATIONS

Chem. Abst., vol. 92, No. 24, p. 51, No. 199477, (1980).

*Primary Examiner*—John Kight, III
*Assistant Examiner*—Nathan M. Nutter
*Attorney, Agent, or Firm*—Wegner & Bretschneider

[57] ABSTRACT

Disclosed herein a process for producing a microcapsule having an excellent solvent-resistance and a thermal stability, and an extremely minute amount of unreacted formaldehyde, comprising the steps of dispersing a substance to be encapsulated into an aqueous solution containing a water-soluble cationic urea resin, at least one prepolymer selected from the group consisting of a melamine-formaldehyde prepolymer, a urea-formaldehyde prepolymer and a melamine-urea-formaldehyde prepolymer and an anionic surfactant and then, adding an acid-catalyst into the thus obtained aqueous dispersion thereby forming a wall membrane which encapsulates the dispersed microparticle of the substance to be encapsulated by polycondensing the prepolymer and the cationic urea resin followed by cross-linking while causing complex coacervation, and adding a monosaccharide into the aqueous dispersion while adjusting the pH of the aqueous dispersion with the addition of a hydroxide of an alkaline earth metal thereby removing the unreacted residual formaldehyde remaining in the aqueous dispersion.

6 Claims, No Drawings

PROCESS FOR PRODUCING A MICROCAPSULE

BACKGROUND OF THE INVENTION

The present invention relates to a process for producing a microcapsule having an excellent solvent-resistance and a thermal stability, and an extremely minute amount of unreacted formaldehyde included within or adhered onto the wall material of the microcapsule by removing the unreacted formaldehyde at the final step of the process, and more in detail, the present invention relates to a process for producing a microcapsule having an excellent solvent-resistance and a thermal stability, and an extremely minute amount of unreacted formaldehyde, comprising the steps of dispersing a substance to be encapsulated into an aqueous solution containing a water-soluble cationic urea resin, at least one prepolymer selected from the group consisting of a melamine-formaldehyde prepolymer, a urea-formaldehyde prepolymer and a melamine-urea-formaldehyde prepolymer and an anionic surfactant and then, adding an acid-catalyst into the thus obtained aqueous dispersion thereby forming a wall membrane which encapsulates the dispersed microparticle of the substance to be encapsulated by polycondensing the prepolymer and the cationic urea resin followed by cross-linking while causing complex coacervation, and adding a monosaccharide into the aqueous dispersion while adjusting the pH of the aqueous dispersion with the addition of a hydroxide of an alkaline earth metal thereby removing the unreacted residual formaldehyde remaining in the aqueous dispersion.

The term "solvent-resistance" herein means the stability of a microcapsule in an organic solvent, for example, an alcohol such as isopropyl alcohol and ethyl alcohol, an ester such as ethyl acetate, a ketone such as methyl ethyl ketone, a hydrocarbon solvent such as kerosene, toluene and xylene, or a vegetable oil such as linseed oil and castor oil.

The present inventors have recently accomplished the inventions relating to respectively a microcapsule having high resistance against moisture, heat and light, which encloses a colour-former solution, obtained by polycondensing at least one of the prepolymers and the water-soluble cationic urea resin in the presence of an anionic surfactant, comprises a polycondensate of a water-soluble cationic urea resin with at least one of the prepolymers selected from the group consisting of a prepolymer of melamine-formaldehyde resin (hereinafter referred to as melamine-formaldehyde prepolymer), a prepolymer of urea-formaldehyde resin (hereinafter referred to as urea-formaldehyde prepolymer) and a prepolymer of melamine-urea-formaldehyde resin (hereinafter referred to as melamine-urea-formaldehyde prepolymer), and a process for producing a microcapsule for pressure-sensitive recording paper, wherein a water-soluble cationic urea resin and at least one of prepolymers selected from the group consisting of melamine-formaldehyde prepolymer, urea-formaldehyde prepolymer and melamine-urea-formaldehyde prepolymer are polycondensed on the surface of a dispersed droplet of a water insoluble material, for example, a solvent containing a colour-former in the presence of an anionic surfactant, while causing complex-coacervation of the droplet.

Although the above-mentioned microcapsule has excellent properties, as in the preparation of the microcapsule by the method from urea-formaldehyde polymer or melamine-folmaldehyde polymer, a large amount of unreacted folmaldehyde inevitably remains in the process system at the stage of completing the formation of the microcapsule.

In consideration of the physiological properties of formaldehyde of stimulating the mucous membrane of nose and eyes and the skin in general, the residual presence of formaldehyde in the process system necessarily causes problems in human health and safety by adhering onto the microcapsule or by polluting the working environment where such microcapsule is handled. Also, in case where the microcapsule is used in a pressure-sensitive recording paper, the microcapsule is required which is excellent in moisture stability, thermal stability and light stability because the pressure-sensitive recording paper tends to be used even under severe environmental conditions. Further, a microcapsule is required which is excellent also in solvent-resistance in preparing a pressure-sensitive recording paper. Also, in case where a free-flowing powder of the microcapsule is produced, the microcapsule is especially preferred which has better solvent-resistance and thermal stability. Consequently, it has been demanded to remove the residual formaldehyde without giving any harmful effect on the wall material of the microcapsule.

As the hitherto proposed methods for removing the residual formaldehyde in the process system of preparing the microcapsule while using folmaldehyde as one of components of the prepolymer, there are, (1) method for selectively absorbing formaldehyde by the use of an absorbent such as sodium sulfite or urea, (2) method of removing formaldehyde by addition of a urea-derivative having 5 or 6 membered ring or 2-oxooxazolidine and a sulfite or a hydrogen sulfite and (3) method of removing formaldehyde by addition of a monosaccharide while keeping the pH of the aqueous dispersion of the microcapsule at 11.0 to 12.5, while adding a hydroxide of alkali metal.

However, in the above-mentioned methods for removing the residual formaldehyde, there are the following defects, in the methods (1) and (2), since the necessary amount of the absorbent is 1 to 5 times by mol of the amount of residual formaldehyde, the presence of a large amount of the absorbent deteriorates the wall membrane of the microcapsule, and in the method (3) since the reaction velocity between the monosaccharide and residual formaldehyde is low at ordinary temperature, it is necessary to heat the system containing residual formaldehyde, and this situation brings about the conspicuous coloration of the aqueous dispersion of the microcapsule (so-called capsule-slurry) and the deterioration of the wall membrane of the microcapsule.

In consideration of these situations, the present inventors have made efforts in studying the methods for removing unreacted formaldehyde remaining in the system for forming microcapsules while using a prepolymer composed of formaldehyde as one of components of the prepolymer, and as a result, the present inventors have found that the amount of residual formaldehyde remaining in the aqueous dispersion of the formed microcapsule can be remarkably reduced without giving any harmful effects on the wall membrane of the microcapsule by the addition of a monosaccharide into the aqueous dispersion of the microcapsule while adjusting the pH of the aqueous dispersion of the microcapsule with the addition of a hydroxide of an alkaline earth metal, and they have accomplished the present invention based on the finding.

SUMMARY OF THE INVENTION

In an aspect of the present invention, there is to provide a process for producing a microcapsule having an excellent solvent-resistance and a thermal stability, and an extremely minute amount of unreacted formaldehyde, comprising the steps of dispersing a substance to be encapsulated into an aqueous solution containing a water-soluble cationic urea resin, at least one prepolymer selected from the group consisting of a melamine-formaldehyde prepolymer, a urea-formaldehyde prepolymer and a melamine-urea-formaldehyde prepolymer and an anionic surfactant and then, adding an acid-catalyst into the thus obtained aqueous dispersion thereby forming a wall membrane which encapsulates the dispersed microparticle of the substance to be encapsulated by polycondensing the prepolymer and the cationic urea resin followed by cross-linking while causing complex coacervation, and adding a monosaccharide into the aqueous dispersion while adjusting the pH of the aqueous dispeion with the addition of a hydroxide of an alkaline earth metal thereby removing the unreacted residual formaldehyde remaining in the aqueous dispersion.

DETAILED DESCRIPTION OF THE INVENTION

The present invention relates to a process for producing a microcapsule having an excellent solvent-resistance, a thermal stability and a moisture stability, and an extremely minute amount of unreacted formaldehyde, comprising the step of removing the unreacted residual formaldehyde remaining in the process system after forming the microcapsule without giving any harmful effects on the wall membrane of the microcapsule thereby greatly reducing the amount of the unreacted residual formaldehyde remaining in the process system and the microcapsule itself.

The characteristic feature of the present invention comprises the steps of dispersing the substance to be encapsulated as minute particles, into an aqueous mixed solution containing a water-soluble cationic urea resin, at least one prepolymer selected from the group consisting of a melamine-formaldehyde prepolymer, a urea-formaldehyde prepolymer and a melamine-urea-formaldehyde prepolymer and an anionic surfactant adding an acid catalyst to the thus obtained aqueous dispersion thereby bringing the prepolymer and the cationic urea resin into polycondensation followed by cross-linking while causing complex coacervation to form a wall membrane which encapsulates the dispersed substance and then adding a monosaccharide into the aqueous dispersion of the thus formed microcapsule while adding a hydroxide of an alkaline earth metal to the aqueous dispersion thereby removing the unreacted residual formaldehyde in the aqueous dispersion.

Concerning the process for producing a microcapsule in the present invention, although one example has been invented by the present inventors, the essentials of the invention is as follows:

The substance to be encapsulated is dispersed in an aqueous mixed solution containing a water-soluble cationic urea resin, at least one prepolymer selected from the group consisting of a melamine-formaldehyde prepolymer, a urea-formaldehyde prepolymer and a melamine-urea-formaldehyde prepolymer and an anionic surfactant, and into the thus obtained aqueous dispersion, an acid-catalyst selected from mineral acids such as hydrochloric acid, nitric acid and phosphoric acid, lower carboxylic acid such as formic acid, acetic acid and citric acid, and acidic salt such as aluminum chloride, ammonium nitrate and ammonium sulfate is added to bring into polycondensation followed by cross-linking at least one prepolymer selected from the group consisting of a urea-formaldehyde prepolymer, a melamine-formaldehyde prepolymer and a urea-melamine-formaldehyde prepolymer and a cationic urea resin while causing complex coacervation by the water-soluble cationic urea resin and the anionic surfactant thereby forming a wall membrane which encapsulate the minute particle of the substance to be encapsulated to form the microcapsule.

The prepolymer used in the present invention includes a urea-formaldehyde prepolymer made of urea and formaldehyde, a melamine-formaldehyde prepolymer made of melamine and formaldehyde, a urea-melamine-formaldehyde prepolymer made of melamine, urea and formaldehyde, and the mixture of a urea-formaldehyde prepolymer with a melamine-formaldehyde prepolymer.

"Melamine-formaldehyde prepolymer" herein indicates any one of a mixture of formaldehyde and at least one of methylol melamines such as mono- to hexamethylol melamine, a mixture of the methylol melamine(s), melamine and formaldehyde, and any oligomer(s) obtained by the further reaction of melamine and formaldehyde, e.g. methylol melamine(s) with the degree of polymerization of 2 to 10 which may be subjected to encapsulation in the form of a transparent colloidal solution obtained by treating the oligomers with hydrochloric acid.

"Urea-formaldehyde prepolymer" of the present invention indicates any one of a mixture of formaldehyde and at least one methylol ureas such as mono- to tetramethylol urea, a mixture of the methylol urea(s), urea and formaldehyde, and any oligomer(s) obtained by the further reaction of urea and formaldehyde, e.g. methylol urea(s) with the degree of polymerization of 2 to 5 and having hydrophilic group(s) which may be used in the form of a transparent colloidal solution.

The molar ratio (R) of formaldehyde to melamine and urea in the raw material used in the preparation of prepolymers, when the melamine-urea-formaldehyde prepolymer is used, is determined according to the following formulae:

$$R = \frac{F}{U + M}$$

$$F = aU + bM$$

wherein F, U and M are respectively the mols of formaldehyde, urea and melamine, and the coefficient a is in the range of 0.6 to 4.0, preferably 1.0 to 3.0, and the coefficient b is in the range of 1.0 to 9.0, preferably 1.6 to 7.0.

The "water-soluble cationic urea resin" indicates a urea-formaldehyde resin prepared in the presence of a cationic modifier. The water-soluble cationic urea resin is easily prepared by adding the modifier to a urea-formaldehyde prepolymer and then carrying polycondensation in the known procedures. The modifier may include tetraethylenepentamine, diaminoethanol, dicyandiamide, diethylaminoethanol, guanylurea and the like.

The "anionic surfactant" of the present invention includes sodium aliphatic carboxylates, higher-alkyl sulfates, sodium alkylallylsulfonates and the like, preferably sodium dodecylbenzenesulfonate.

The pH and the temperature of the aqueous dispersion containing the prepolymer to which the acid catalyst is added under a gentle stirring are maintained in the respective range of 2.6 to 6.0 and 15° to 60° C.

As has been described above, in order to form a favorable wall membrane of microcapsules in the step of microcapsule formation, it is necessary to exist a large amount of formaldehyde into the aqueous solution containing the raw materials, and accordingly, a considerable amount of unreacted formaldehyde remains in the reaction system, the unreacted residual formaldehyde amounts to 1 to 1.5 by weight of the aqueous dispersion of microcapsule under certain circumstances.

Although in the cases where the microcapsule is used as a powdery product, the amount of the unreacted residual formaldehyde is considerably reduced by separating and washing the microcapsule from the aqueous dispersion, some amount of formaldehyde inevitably remains within the wall membrane of the microcapsule or on the wall membrane by adhesion or adsorption.

Consequently, in the present invention, a monosaccharide is added to the aqueous dispersion of microcapsule (after the formation of the microcapsule) while adjusting the pH of the aqueous dispersion in a range of 10.5 to 12.5 by the addition of a hydroxide of an alkaline earth metal under a gentle stirring to remove formaldehyde in the system while utilizing the condensation of formaldehyde with the monosaccharide. In the case where the pH is lower than 10.5, the velocity of condensation is reduced resulting in requiring a longer time for removing the residual formaldehyde, and on the other hand, in the case where the pH is higher than 12.5, the aqueous dispersion of microcapsule is coloured and the wall membrane of the microcapsule is deteriorated. In addition, of the hydroxides of alkaline earth metals, calcium hydroxide is preferable because its reactivity is large and it does not show any side effects such as the coloration of the aqueous dispersion and the deterioration of the wall membrane of the microcapsule with its merit of low price.

Although it is natural that the higher the reaction temperature, the larger the reaction velocity, in consideration of the possible coloration of the aqueous dispersion of microcapsule, the reaction temperature is preferably 20° to 70° C. The time period for the reaction depends on the temperature of reaction, the amount of monosaccharide and the pH of the reaction system, however, it takes 10 min. to 20 hours for completion in usual cases.

As the monosaccharide for use in removing the residual formaldehyde, fructose, glucose and sorbose are enumerable, and they are respectively used singly or as a mixture of more than two kinds, and fructose is particularly preferable.

The amount of the monosaccharide for use in removal of the residual formaldehyde may be 5 to 300 parts by weight, preferably 20 to 200 parts by weight to 100 parts by weight of the unreacted residual formaldehyde in the aqueous dispersion of the microcapsule. The smaller amount of the monosaccharide causes the elongation of the reaction time, and on the other hand, the larger amount thereof causes the coloration and the excessive viscosity-raising of the aqueous dispersion of microcapsule.

According to the process of the present invention, since the wall membrane of the microcapsule is formed by the polycondensation and cross-linking of at least one prepolymer selected from urea-formaldehyde prepolymer, melamine-formaldehyde prepolymer and urea-melamine-formaldehyde prepolymer, and the cationic urea resin while causing complex-coacervation by the water-soluble cationic urea resin and the anionic surfactant, it has become possible to obtain an extremely stable microcapsule and to remove the residual formaldehyde remaining in the aqueous dispersion without being accompanied by the coagulation of microcapsules and the deterioration of the wall membrane of the microcapsule.

In this connection, Japanese Patent Application Laying-Open No. 55-18218 (1980) disclosing the process for producing a microcapsule comprising the wall membrane made of urea-formaldehye polymer or melamine-formaldehyde polymer, which discloses a step of removing the residual formaldehyde by addition of monosaccharide while adjusting the pH of the aqueous dispersion of the microcapsule, describes that the use of a hydroxide of an alkaline earth metal such as calcium and magnesium together with the monosaccharide is not favourable because of its harmful effect on the wall membrane of the microcapsule.

On the contrary, in the present invention, the removal of the residual formaldehyde is smoothly carried out without giving any harmful effects on the wall membrane of the microcapsule by the method of adding a monosaccharide to the aqueous dispersion of the microcapsule while adjusting the pH of the aqueous dispersion by the addition of a hydroxide of calcium, magnesium or barium. In this point, the present invention is quite unique.

Since the amount of the residual formaldehyde in and on the microcapsule obtained according to the present invention is quite small and the microcapsule of the present invention have a better solvent-resistance and thermal stability as are shown in Examples, the aqueous dispersion of the microcapsule and the dried microcapsule prepared by the process of the present invention can be profitably applicable in various fields such as manufacture of pressure-sensitive recording papers, of agricultural chemicals, of perfumes, and the like, wherein encapsulate substance is profitably prepared, used or commercialized.

The present invention will be more precisely explained while referring to Examples as follows.

However, the present invention is not restricted to Examples under mentioned. From the foregoing description, one skilled in the art can easily ascertain the essential characteristics of this invention, and without departing from the spirit and scope thereof, can make various changes and modifications of the invention to adapt it to various usages and conditions.

EXAMPLE 1

To begin with, a urea-formaldehyde prepolymer aqueous solution was prepared by mixing 300 g of urea and 3 g of triethanolamine with 730 g of an aqueous 37% solution of formaldehyde and heating the mixture at 70° C. for 60 min. After adjusting the pH of the mixture, to 5.0, of 100 g of the thus prepared prepolymer solution, 20 g of an aqueous 38% by weight solution of a cationic urea resin (Uramine ® P-1500, made by MIT- SUITOATSU Company, Japan), 200 g of water and 10 g of an aqueous 10% solution of triethanolamine, with aqueous 10% solution of citric acid, an aqueous solution (hereinafter referred to as A-solution) was prepared by adding 3 g of an aqueous 10% solution of sodium alkylbenzenesulfonate (Neoprex ®, made by KAO-ATLAS Company, Japan) to the mixed solution.

An oil solution (hereinafter referred to as B-solution) was separately prepared by dissolving 30 g of crystal violet lactone in 970 g of diisopropylnaphthalene (DIPN), and 150 ml of B-solution was emulsified into A-solution in a homogenizer to be particles of 2 to 8 microns in average diameter. Then the emulsion was heated to 50° C. under a gentle stirring and the pH of the emulsion was adjusted to 3.6 by the addition of an aqueous 10% solution of citric acid to bring the prepolymer in the emulsion into reaction. At the time when the viscosity-raise of the emulsion was observed, 600 g of water was slowly added to the emulsion, and the reaction was continued for about one hour. After adding the aqueous 10% solution of citric acid to the reaction product to adjust the pH thereof to 2.8 and stirring thereof for one hour, the emulsion was cooled to room temperature, and the stirring was continued further for 10 hours to obtain a slurry of microcapsules for pressure-sensitive recording paper (hereinafter referred to Capsule-slurry C) containing the unreacted residual formaldehyde at a concentration of 9900 ppm (w/w) determined by the acetylacetone method (JIS L 1041, 5.2-1.2.2).

A mixture of 5 g of the thus obtained Capsule-slurry C and 2 g of an aqueous 10% solution of polyvinyl alcohol (product of complete saponification of polyvinyl acetate) was painted on a sheet of typewriting paper at a rate of about 6.5 g of solid material on one m² of the sheet and dried for one min at 105° C. The amount of the residual formaldehyde in the thus painted sheet of paper was 2300 ppm by the same method of determination.

After collecting the microcapsule by filtration of 50 g of Capsule-slurry C and washing the microcapsule with water, the washed microcapsule was dried at 40° C. under a reduced pressure to obtain 10 g of free-flowing powdery microcapsule (hereinafter referred to as Capsule-powder (D) containing 980 ppm of residual formaldehyde determined by the acetylacetone method.

Into another 100 parts by weight of Capsule-slurry C at 40° C., 1.5 parts by weight of calcium hydroxide was added to adjust the pH of the mixture to 11.8 while stirring Capsule-slurry C, and then 0.4 part by weight of fructose (corresponding to about 40% by weight of the residual amount of formaldehyde in Capsule-slurry C) was added to react with the residual formaldehyde for one hour. After finding the yellowish colouring of Capsule-slurry C, the stirring was discontinued and the slurry was cooled to room temperature. The thus treated slurry did not contain any mutual coagulant of microcapsule and the amount of formaldehyde in the treated slurry was 145 ppm. After painting the thus treated Capsule-slurry C on a sheet of typewriting paper in the same manner as in the case of the untreated Capsule-slurry C, the amount of residual formaldehyde in the painted sheet was 35 ppm by the acetyl-acetone method.

After collecting the microcapsule by filtration of the thus treated Capsule-slurry C and washing the collected microcapsule with water, the washed microcapsule was dried at 40° C. under a reduced pressure. The residual amount of formaldehyde in the thus dried microcapsule was 20 ppm by the acetylacetone method.

EXAMPLE 2

Into 200 parts by weight of Capsule-slurry C obtained in Example 1 (containing 9900 ppm of residual formaldehyde determined by the acetylacetone method), 3.6 parts by weight of calcium hydroxide was added under agitation to adjust the pH of the slurry to 11.9, and after dividing the mixture equally into two parts, 0.4 part by weight of fructose was added to the one of the parts, and 1.0 part by weight of fructose was added to the other part, and then the reaction was carried out in both parts as in Example 1.

The amount of residual formaldehyde in the thus treated capsule-slurry, and that in the sheet of typewriting paper painted with the capsule-slurry further treating with an aqueous 10% solution of citric acid to pH of 8.3 in the same procedures in Example 1 are shown in Table 1 below. As the control, the amount of residual formaldehyde in Capsule-slurry C treated only with the addition of 1.8 parts by weight of calcium hydroxide into 100 parts by weight of Capsule-slurry C to adjust the pH thereof to 11.9 (without adding fructose), and that in the painted sheet of typewriting paper with the thus treated capsule-slurry are also shown in Table 1.

TABLE 1

| Classification | Amount of fructose added (part by weight) | Reaction time (min) | Amount of residual formaldehyde determined by the acetylacetone method | |
|---|---|---|---|---|
| | | | in capsule-slurry (ppm) | in painted sheet (ppm) |
| Present invention | 0.4 | 30 | 235 | 39.9 |
| | 1.0 | 30 | 96 | 30.8 |
| Control | 0 | 1800 | 800 | 85.0 |

Note: The pH of capsule-slurry after adjusting by the addition of citric acid was 8.3 in every case.

As is seen in Table 1, the amount of residual formaldehyde in the capsule-slurry and in the painted sheet of paper with the capsule-slurry according to the present invention are remarkably smaller than those of control.

EXAMPLE 3

A part of Capsule-slurry C obtained in Example 1 (containing 9900 ppm of unreacted residual formaldehyde determined by the acetylacetone method) was divided into six equal portions, and to each 100 parts by weight of the divided portion an amount of calcium hydroxide was added to adjust the pH shown in Table 2, and then, after adding glucose, sorbose or fructose as shown also in Table 2, the respective portions were brought into reaction under the conditions also shown in Table 2. The amount of residual formaldehyde in each of the thus treated capsule-slurries, and that in each of the painted sheets of typewriting paper with the respective capsule-slurries in the same manner as in Example 2 are shown also in Table 2.

TABLE 2

| No. of Division | pH of Capsule-slurry | Kind and amount of monosaccharide added (part by wt.) | | Reaction conditions | | Amount of residual formaldehyde (ppm) in (determined by the acetylacetone method) | |
|---|---|---|---|---|---|---|---|
| | | | | temp. (°C.) | hour | Capsule-slurry | Painted paper |
| 1 | 11.9 | glucose | 0.5 | 40 | 1 | 420 | 64.5 |
| 2 | 11.9 | sorbose | 0.5 | 40 | 1 | 380 | 50.8 |
| 3 | 10.8 | fructose | 0.5 | 70 | 2 | 430 | 59.3 |
| 4 | 11.95 | fructose | 0.3 | 20 | 19 | 570 | 38.1 |
| 5 | 12.2 | fructose | 0.2 | 70 | 0.2 | 45 | 15.0 |
| 6 | 12.2 | fructose | 0.4 | 40 | 0.4 | 32 | 30.5 |

As are seen in Table 2, the amount of residual formaldehyde in the capsule-slurries subjected to the treatment of removing unreacted formaldehyde according to the present invention, and that in the painted sheets of typewriting paper with the thus-treated capsule-slurry are remarkably small, and all the amounts of residual formaldehyde in the respective painted sheets were less than the upper limit of the torelance standard of the commercial materials (of less than 70 ppm).

In Addition, although a slight yellowing was seen in the capsule-slurries of Divisions 5 and 6, there were no inconveniences in the practical utilization of such capsule-slurries without any mutual coagulation of the microcapsules themselves and any deterioration in quality.

EXAMPLE 4

A yellowish brown solution was prepared by dissolving 3 parts by weight of calcium hydroxide and 8 parts by weight of fructose into 30 parts of water at 40° C. under agitation. Into 100 parts by weight of the Capsule-slurry C which has been obtained in Example 1 and previously adjusted to pH 11.5 by the addition of calcium hydroxide (content of formaldehyde of 9900 ppm), 4.1 parts by weight of the yellowish brown solution was added and they were brought into reaction while stirring for 30 min at 40° C. the amount of unreacted formaldehyde in the thus prepared capsule-slurry was 56 ppm. The amount of residual formadehyde in the sheet of typwriting paper painted with the capsule-slurry was 26.8 ppm determined by the acetylacetone method.

EXAMPLE 5

Into 100 parts by weight of Capsule-slurry C obtained in Example 1, magnesium hydroxide was added to adjust the pH of the mixture to 11.8, and 0.4 part by weight of fructose was added to the thus treated Capsule-slurry C to bring the mixture into reaction for one hour, the amount of unreacted formaldehyde in the thus reacted slurry being 250 ppm and that in the painted sheet of paper with the thus reacted slurry being 70 ppm determined by the acetylacetone method.

COMPARATIVE EXAMPLE 1

In the present Comparative Example, a case where sodium hydroxide, a hydroxide of an alkali metal was used instead of the hydroxide of an alkaline earth metals according to the present invention was shown as follows:

Into 100 parts by weight of Capsule-slurry C (containing 9900 ppm of unreacted formaldehyde determined by the acetylacetone method) obtained in Example 1, an aqueous 10% solution of sodium hydroxide was added to adjust the pH of the mixture to the value shown in Table 3, and glucose was added in an amount shown in Table 3 to the slurry to bring the mixture into reaction for one hour at 40° C. The amount of unreacted formaldehyde in the thus treated capsule-slurry and that in the painted sheet of typewriting paper in the same manner as in Example 2 with each of the thus treated capsule-slurries are shown in Table 3.

TABLE 3

| pH of Capsule-slurry | Amount of glucose added (part by weight) | Amount of residual formaldehyde (ppm) in (determined by the acetylacetone method) | |
|---|---|---|---|
| | | Capsule-slurry | painted sheet |
| 11.9 | 0.5 | 6000 | 850 |
| 12.2 | 5 | 1966 | 344 |
| 11.5 | 7 | 2900 | 339 |

As seen in Table 3, in the cases where a hydroxide of an alkali metal such as sodium hydroxide was used for adjusting the pH of the aqueous dispersion of microcapsules according to the process of the present invention except for using a hydroxide of an alkaline earth metal, the effect of removing the residual formaldehyde was inferior as compared to the case where a hydroxide of an alkaline earth metal, particularly the content of formaldehyde in the painted paper was higher than the upperlimit of the torelance standard.

EXAMPLE 6

By adding 162 g of 37% aqueous formaldehyde solution which had been adjusted to pH 9.0 by aqueous 2% sodium hydroxide solution to 63 g of melamine, the mixture was brought into reaction at 70° C. In this case, as soon as the melamine was dissolved into the solution, 225 g of water was added to the solution and stirred for 3 min. to obtain an aqueous solution of a melamine prepolymer and formaldehyde (hereinafter referred to as "M4F").

Separately, 60 g of urea was added to 146 g of aqueous 37% formaldehyde solution adjusted to pH 8.5 by the addition of triethanolamine and the mixture was brought into reaction at 70° C. for one hour to obtain an aqueous solution of an urea-formaldehyde prepolymer (hereinafter referred to as "U 1.8F").

Further, separately, 162 g of 37% aqueous formaldehyde solution and 60 g of urea were mixed under agitation, and triethanolamine was added to the mixture to adjust its pH to 8.8, and then the mixture was brought into reaction at 70° C. for 30 min. To the thus obtained reaction mixture, 144 g of water and 6 g of tetraethylenepentamine were added, and after adding aqueous 15% hydrochloric acid to the reaction mixture to adjust its pH to 3.0 under agitation and at 70° C., the mixture was brought into reaction for one hour. In this case, the reduction of pH of the reactant was compensated by adding aqueous 10% sodium hydroxide solution to maintain the pH at 3.0 and the reaction was continued at 55° C. At the time when the viscosity of the reactant became 200 cps, the reactant was neutralized by the addition of aqueous 10% sodium hydroxide solution and then 2400 g of water to the reaction mixture to obtain an aqueous solution of a water-soluble cationic urea resin.

The thus obtained prepolymers M4F, U 1.8F, the cationic urea resin, water and triethanolamine were admixed in the weight ratio of 100:50:158:62.1, and after adjusting pH of the mixture to 5.2 by adding aqueous 10% citric acid solution to the mixture, 3 g of aqueous 10% Neoprex ® solution (an aqueous solution of sodium alkylbenzenesulfonate, prepared by KAO-ATLAS Company, Japan) was added to 371 g of the mixture.

To the thus prepared mixture, 150 g of a solution of a colour-former, and the mixture was subjected to a homogenizer to obtain an aqueous dispersion of particles of 2 to 8 microns in average diameter. Then the dispersion was maintained at a temperature of 30° C. while slowly stirring the dispersion and its pH was adjusted to 3.6 by an addition of aqueous 10% citric acid solution. After one hour, 200 g of water was added to the aqueous dispersion and further after one hour, the pH of the dispersion was adjusted to 2.8, the dispersion being stirred further 2 hours. Then by warming the dispersion to 40° C. and by stirring the dispersion for 3 hours, the microcapsulation was completed in the dispersion. The residual amount of formaldehyde still remaining in the thus obtained capsule-slurry (hereinafter referred to as Capsule-slurry D) was 8000 ppm determined by "acetylacetone method".

In the next place, into 50 parts by weight of the thus obtained Capsule-slurry D, 0.75 part by weight of calcium hydroxide was added to adjust the pH of Capsule-slurry D to 11.9, and then, 0.2 part by weight of fructose was added to the resultant slurry and the mixture was stirred for 30 min. while maintaining the temperature of the whole mixture at 60° C.

After cooling Capsule-slurry D thus treated to room temperature, microcapsules in Capsule-slurry D were collected by centrifugation, washed with water and dried in a warm air flow at 50° C. for 16 hours. The residual amount of formaldehyde in the thus obtained microcapsules was 35 ppm by determination in the acetylacetone method.

The results of tests on the stability of the thus obtained microcapsules under hot-and humid environments, the resistance of the thus obtained microcapsules to hot water, the solvent-stability of the microcapsules after subjecting to the hot-and humid environmental test and the solvent-resistance of the microcapsules after subjecting to the hot-water resistance test are shown in Table 4. The test methods are shown in the note of Table 4.

COMPARATIVE EXAMPLE 2

After adding aqueous 10% sodium hydroxide solution to 50 parts by weight of Capsule-slurry D prepared in Example 6 to adjust its pH to 11.9, 0.2 part by weight of fructose was added to the resultant slurry, and the whole system was stirred for 30 min at 60° C. After cooling the thus treated capsule-slurry to room temperature, the microcapsules in the capsule-slurry were collected by centrifugation, and the collected microcapsules were washed with water and dried in a warm air flow at 50° C. for 16 hours. The residual amount of formaldehyde in the thus dried microcapsules determined by the acetylacetone method was 850 ppm. The results of tests on the stability of the thus obtained microcapsules under hot-and humid environments, the resistance of the thus obtained microcapsules to hot water, the solvent resistance of the microcapsules after subjecting to the hot-and humid environmental test and the solvent-resistance of the microcapsules after subjecting to the hot-water resistance test are shown in Table 4.

EXAMPLE 7

Into a mixture of 25 g of Uramine ®P 1500 (a cationic urea resin, prepared by MITSUI-TOATSU Company, Japan), 100 g of the prepolymer U 1.8F prepared in Example 6, 180 g of water and 1 g of triethanolamine, aqueous 10% citric acid solution was added to adjust the pH of the mixture to 5.5, and further 3.7 g of aqueous 10% Neoprex solution (refer to Example 6) was added to the mixture. After adding 150 g of an insecticide, fenitrothion into the thus treated mixture, the whole mixture was subjected to a homogenizer to obtain an aqueous dispersion of microparticles with an average diameter of 5 to 10 microns, and while maintaining the aqueous dispersion at 35° C. under gentle stirring, aqueous 10% citric acid solution was added to the dispersion to bring the pH of the aqueous dispersion at 3.5. After maintaining the temperature of dispersion at 35° C. for one hour, 150 g of water was added to the dispersion and the mixture was stirred as it was for 2 hours, and then, aqueous 10% citric acid solution was again added to the mixture to bring its pH to 3.0, while continuously stirring the mixture. After one hour of stirring, 150 g of water was again added to the whole system and the stirring was continued for additional 15 hours. Then, the microcapsulation was completed. The residual amount of formaldehyde in the thus completed capsule-slurry was determined by the acetylacetone method to be 9200 ppm.

In the next place, after adding 0.75 part by weight of calcium hydroxide to 50 parts by weight of the thus obtained capsule-slurry to adjust the pH of the capsule-slurry to 11.8 and further adding 0.4 part by weight of fructose to the resultant slurry, the resultant capsule-slurry mixture was stirred for 15 min at 60° C. Then, the capsule-slurry was cooled to room temperature, and subjected to centrifuge to collect the microcapsules in the slurry, and the collected microcapsules were washed with water and dried in a warm air flow at 50° C. for 16 hours to obtain the dried microcapsules containing the residual formaldehyde of 51 ppm (analysis by the acetylacetone method).

EXAMPLE 8

After adjusting the pH of a mixture, to 5.0, of 140 g of the water-soluble cationic urea resin prepared in Example 6, 200 g of the prepolymer M4F prepared in Example 6, 80 g of water and 1 g of triethanolamine with an addition of aqueous 10% citric acid solution to 5.0, 3 g of aqueous 10% Neoprex solution (refer to Example 6) and 150 g of a colour-former solution were added to the mixture. Then, the whole system was subjected to a homogenizer to be an aqueous dispersion of droplets of 5 to 10 microns in average diameter. While maintaining the aqueous dispersion at 40° C. under a gentle stirring, aqueous 10% citric acid solution was added to the dispersion to adjust pH thereof at 3.0 and then, 100 g of water was added to the dispersion. The microcapsulation was completed by the further stirring of 15 hours.

The residual amount of formaldehyde in the thus obtained capsule-slurry was determined by the acetylacetone method to be 8500 ppm.

In the next place, after adding 0.75 part by weight of calcium hydroxide to 50 parts by weight of the thus obtained capsule-slurry to adjust the pH of the slurry to 11.9, 0.2 part by weight of fructose was added to the resultant capsule-slurry and the slurry was stirred for 30 min at 60° C. After cooling the capsule-slurry to room temperature, microcapsules in the thus-treated capsule-slurry were collected by centrifugation, washed with water and dried in a warm air flow at 50° C. for 16 hours. The residual amount of formaldehyde in the thus obtained microcapsules was determined by the acetylacetone method to be 43 ppm. The results of tests on the stability of the microcapsules under hot-and humid environmental conditions, the resistance to hot water of the microcapsules, the solvent-resistance of the microcapsules after subjecting the microcapsules to the hot-and-humid environmental conditions and the solvent-resistance of the microcapsules after subjecting the microcapsules to the hot water test are shown in Table 4.

TABLE 4

| | Test Results on Microcapsules | | | |
|---|---|---|---|---|
| | Test 1 | | Test 2 | |
| Specimen | Stability under hot- and humid conditions (%) | Solvent- resistance after Test 1 (%) | Resistance to hot- water (%) | Solvent- resistance after Test 2 (%) |
| Example 6 | 2.9 | 100 | 5.3 | 100 |
| Example 8 | 3.0 | 100 | 5.2 | 99.8 |
| Comparative Example 2 | 4.0 | 98.2 | 9.3 | 95.5 |

Note:
Test methods are as follows:

Stability under hot-and humid environmental conditions

About one gram of the thus prepared microcapsules is introduced into a glass cylindrical filter, and the filter is kept in a thermostat kept at 20° C. and relative humidity of 60% for one hour, and the weight of the filter containing the microcapsules ($W_o$) is accurately determined.

In the next place, the filter containing the microcapsules is placed in a chamber kept at 60° C. and relative humidity of 100% for 8 hours. After removing the filter from the chamber, the filter is dried in a hot air flow at 105° C. for 16 hours. Then, the filter is transferred to the thermostat kept at 20° C. and relative humidity of 60%, and after placing for one hour, the weight of the filter containing the microcapsules ($W_1$) is accurately determined, and the weight of the filter ($W_2$) is accurately determined.

The percentage of weight-loss is calculated according to the following formula:

$$\text{Weight loss}(\%) = \frac{W_0 - W_1}{W_0 - W_2} \times 100$$

The microcapsules showing the smaller weight loss percentage are superior in the stability under hot-and humid environmental conditions.

Resistance to Hot water

About one gram of the thus prepared microcapsules is introduced into a glass cylindrical filter, and after keeping the filter containing the microcapsules in a thermostat kept at 20° C. and a relative humidity of 60% for one hour, the weight of the filter containing the microcapsules ($W_o$) is accurately determined. In the next place, after immersing the filter containing the microcapsules into boiling water for 4 hours, it is removed from boiling water and dried in a hot air flow at 105° C. for 16 hours. Then the filter containing the microcapsules is transferred into the thermostat kept at 20° C. and a relatively humidity of 60%, and after keeping for one hour, the weight of the filter containing the microcapsules ($W_H$) is accurately determined, and the weight of the filter ($W_2$) is accurately determined.

The percentage weight loss is calculated according to the following formula:

$$\text{Weight loss}(\%) = \frac{W_0 - W_H}{W_0 - W_2} \times 100$$

The microcapsules showing the smaller weight loss percentage is superior in the resistance to hot water.

Solvent-Resistance

Ten grams of the thus prepared microcapsules are ground in a mortar and 200 ml of toluene is added thereto, and the system is kept standing. Then the supernatant liquid is transferred into a 500-ml flask. The remaining microcapsules in the mortar are ground again and after adding 200 ml of toluene thereto, the system is well mixed and the mixture is transferred to the 500-ml flask. The mortar and the pestle are washed well with toluene, and the washings are transferred into the 500-ml flask. Toluene is added to the solution in the 500-ml flask to make the whole volume of the liquid in the flask to 500 ml. The amount of the solvent used for making the colour-former, such as diisopropylnaphthalene is determined by gas chromatography, the amount being referred to as A.

On the other hand, 10 g of the same microcapsules are placed in a 100-ml conical flask with a glass stopper, and after adding 50 g of a test solvent, namely, mixture of butyl acetate and isopropyl alcohol (1:1), respectively, into the flask, the flask is allowed to stand for 30 hours at 35° C. Then, the microcapsules in the flask are removed from the flask and washed well with the test solvent. This procedure of solvent-extraction is repeated once more, and the amount of the solvent used for making the colour-former is determined by gas chromatography, the amount being referred to as B.

The retaining degree of the core material after immersing the capsules into a solvent is calculated by the following formula:

$$\text{Retaining degree }(\%) = B/A \times 100$$

The solvent-resistance of the microcapsules is better as the reacting degree is higher.

What is claimed is:

1. A process for producing a microcapsule comprising the steps of:

(a) dispersing a substance to be encapsulated within the wall membrane of said microcapsule in an aqueous solution containing a water-soluble cationic urea resin, an anionic surfactant and at least one prepolymer selected from the group consisting of,
  (i) prepolymer of urea-formaldehyde resin,
  (ii) prepolymer of melamine-formaldehyde resins, and
  (iii) prepolymer of melamine-urea-formaldehyde resin;
(b) bringing said prepolymer and said cationic urea resin into polycondensation and cross-linking while
(c) causing complex-coacervation of said aqueous dispersion by adding an acid-catalyst thereby forming said wall membrane; then
(d) adding 5 to 300 parts by weight of a monosaccharide selected from the group consisting of
  (i) fructose,
  (ii) glucose, and
  (iii) sorbose
to said aqueous dispersion of said microcapsule corresponding to 100 parts by weight of residual formaldehyde remaining in said aqueous dispersion of said microcapsule; while
(e) adjusting the pH of said aqueous dispersion of said microcapsule to 10.5–12.5 by an addition of hydroxide of an alkaline earth metal at a temperature of 20° to 70° C. thereby removing the residual formaldehyde remaining in the system.

2. A process according to claim 1, wherein said prepolymer is a prepolymer of melamine-formaldehyde.

3. A process according to claim 1, wherein said prepolymer is a prepolymer of urea-formaldehyde.

4. A process according to claim 1, wherein said prepolymer is a mixture of a prepolymer of melamine-formaldehyde and a prepolymer of urea-formaldehyde.

5. A process according to claim 1, wherein said prepolymer is a prepolymer of melamine-urea-formaldehyde.

6. A process according to claim 1, wherein said alkaline earth metal is calcium.

* * * * *